(12) United States Patent
Yang et al.

(10) Patent No.: US 12,196,747 B2
(45) Date of Patent: Jan. 14, 2025

(54) MULTI-MICROORGANISM DETECTION SYSTEM

(71) Applicant: GIST (Gwangju Institute of Science and Technology), Gwangju (KR)

(72) Inventors: Sung Yang, Gwangju (KR); Young Ran Yun, Gwangju (KR); Taek Eon Jeong, Gwangju (KR)

(73) Assignee: GIST(Gwangju Institute of Science and Technology), Gwangju (KR)

( * ) Notice: Subject to any disclaimer, the term of this patent is extended or adjusted under 35 U.S.C. 154(b) by 764 days.

(21) Appl. No.: 17/403,646

(22) Filed: Aug. 16, 2021

(65) Prior Publication Data
US 2022/0170922 A1 Jun. 2, 2022

(30) Foreign Application Priority Data
Nov. 27, 2020 (KR) .......................... 10-2020-0162664

(51) Int. Cl.
*G01N 33/543* (2006.01)
*B03C 5/00* (2006.01)
(Continued)

(52) U.S. Cl.
CPC ....... *G01N 33/54326* (2013.01); *B03C 5/005* (2013.01); *G01N 1/4077* (2013.01);
(Continued)

(58) Field of Classification Search
CPC .. B03C 1/01; B03C 1/288; B03C 1/30; B03C 5/005; B03C 5/026; G01N 27/44786;
(Continued)

(56) References Cited

U.S. PATENT DOCUMENTS 8,293,089 B1 * 10/2012 James .................... B03C 1/288
204/660

OTHER PUBLICATIONS

C. W. Shields IV et al., "Microfluidic cell sorting: a review of the advances in the separation of cells from debulking to rare cell isolation", Lab on a Chip, vol. 15, Jan. 6, 2015, pp. 1230-1249, doi: 10.1039/c4lc01246a.

(Continued)

*Primary Examiner* — Gurpreet Kaur
(74) *Attorney, Agent, or Firm* — Studebaker & Brackett PC

(57) ABSTRACT

The present invention relates to a multi-microorganism detection system, and more particularly, to a multi-microorganism detection system using a dielectrophoresis force. Provided is a rapid and accurate multi-microorganism detection system. Microorganisms are concentrated at a high throughput using DEP after synthesizing the microorganisms and fluorescent magnetic particles, and when a complex in which the fluorescent magnetic particles are bound to the microorganisms passes through a detection unit by moving only the microorganisms to the detection unit after separating the magnetic particles from the complex (i.e., the microorganisms to which the magnetic particles are bound) using a DEP force, a fluorescence signal of a specific wavelength band is generated according to the type of the fluorescent magnetic particle and the concentration of the microorganisms according to the type of microorganism is measured by measuring and analyzing the fluorescence signal.

9 Claims, 5 Drawing Sheets

(51) Int. Cl.
 *G01N 1/40* (2006.01)
 *G01N 21/64* (2006.01)
 *G01N 27/447* (2006.01)
 *G01N 33/569* (2006.01)

(52) U.S. Cl.
 CPC ... *G01N 21/6428* (2013.01); *G01N 27/44721* (2013.01); *G01N 27/44786* (2013.01); *G01N 33/569* (2013.01); *G01N 2021/6439* (2013.01)

(58) Field of Classification Search
 CPC ....... G01N 27/44721; G01N 33/54326; G01N 33/54333; G01N 33/569
 See application file for complete search history.

(56) References Cited

OTHER PUBLICATIONS

C. M. Yousuff et al., "Microfluidic Platform for Cell Isolation and Manipulation Based on Cell Properties", Micromachines, vol. 8, No. 15, Jan. 4, 2017, pp. 1-15, doi: 10.3390/mi8010015.
An Office Action mailed by the Korean Intellectual Property Office on Nov. 17, 2022, which corresponds to Korean Patent Application No. 10-2020-0162664 and is related to U.S. Appl. No. 17/403,646.

* cited by examiner

MULTI-MICROORGANISM DETECTION SYSTEM

CROSS-REFERENCE TO RELATED APPLICATION

This application claims priority to and the benefit of Korean Patent Application No. 10-2020-0162664, filed on Nov. 27, 2020, the disclosure of which is incorporated herein by reference in its entirety.

BACKGROUND

1. Field of the Invention

The present invention relates to a multi-microorganism detection system, and more particularly, to a multi-microorganism detection system using a dielectrophoresis force.

2. Discussion of Related Art

Dielectrophoresis was defined by Herbert A. Pohl in 1951. Dielectrophoresis refers to a phenomenon in which a directional force is exerted on a particle due to a dipole induced in the particle when the particle is placed in a non-uniform electric field. The strength of a force may vary depending on electrical and dielectric properties of a particle and a medium, a frequency of an alternating current electric field, and the like, and the movement of the particle may be controlled using this force. Since dielectrophoresis techniques are applicable to any polarizable particle, the dielectrophoresis may be used for the movement, separation, and collection of various biological particles including cells.

The conventional procedures used for detecting microorganisms typically involve culturing samples. In this case, a target microorganism may be cultured in a culture medium which is specific to the target microorganism. In the case of the most commonly used culture method, there is a problem in that it takes a long time because 24 hours or more is required for the culturing of microorganisms.

In addition, immunochromatography and reverse transcription polymerase chain reaction (RT-PCR) also have problems in that the detection of microorganisms takes a long time and because a small amount of sample is used, when the concentration of microorganisms is low, accurate detection is difficult and there is a high possibility of showing an error result.

Therefore, a pretreatment process for increasing the concentration of microorganisms is required for accurate detection, but a concentration function and an integrated sensor are very limited, and the conventional integrated sensor has a problem in that a processing speed is very low.

SUMMARY OF THE INVENTION

The present invention is directed to providing a multi-microorganism detection system using a dielectrophoresis (DEP) force.

The present invention is also directed to providing a device for detecting a microorganism using a DEP force corresponding to a magnetic particle bound to a microorganism.

Objects of the present invention are not limited to the above-described objects and other objects which have not been described may be clearly understood from the following description.

According to an aspect of the present invention, there is provided a multi-microorganism detection system including a concentration unit including a magnetic member for generating a magnetic force and configured to concentrate a magnetic particle-microorganism complex using the magnetic force, a separation unit configured to separate magnetic particles from the magnetic particle-microorganism complex using the magnetic force and a DEP force, and a detection unit configured to detect the magnetic particle-microorganism complex using a fluorescence signal of the magnetic particles.

The concentration unit may include a first injection unit configured to inject a sample solution containing the magnetic particles and the magnetic particle-microorganism complex, a second injection unit configured to inject a sheath fluid, a concentration channel through which the sheath fluid containing the magnetic particle-microorganism complex is moved, a first discharge unit configured to transmit the sheath fluid containing the magnetic particle-microorganism complex to the separation unit, and a second discharge unit configured to discharge the sample solution.

The concentration channel may be located parallel to the magnetic member, and the magnetic particle-microorganism complex may be moved along one side surface of the concentration channel due to the magnetic force.

The separation unit may include a third injection unit configured to inject a sheath fluid containing the magnetic particles and the magnetic particle-microorganism complex, a separation channel through which the magnetic particles and the magnetic particle-microorganism complex are moved, a third discharge unit configured to discharge the separated magnetic particle, and a fourth discharge unit configured to transmit the separated magnetic particle-microorganism complex to a detection channel.

One end of the separation channel may be coupled to the third injection unit, the other end of the separation channel may be coupled to the third discharge unit and the fourth discharge unit, a width of the separation channel may be increased in a direction from the one end thereof and then may be decreased in a direction toward the another end.

The separation channel may have one side having a quadrilateral shape which is disposed parallel to the magnetic member, the third injection unit may be coupled to an end portion of one side of the separation channel close to the magnetic member, and the third discharge unit and the fourth discharge unit may be coupled to the separation channel at a diagonal position of the third injection unit.

The third discharge unit and the fourth discharge unit may be vertically located at the other end of the separation channel.

The multi-microorganism detection system may further include a patterned electrode located below the separation channel, and the electrode may be patterned while forming a predetermined angle, preferably 90 degrees, with an injection direction of the magnetic particle-microorganism complex in the separation channel.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

While the present invention may have various modifications and alternative forms, specific embodiments thereof are shown by way of example in the accompanying drawings and will be described herein in detail.

Various features of the present invention disclosed in claims may be better understood in consideration of the drawings and detailed descriptions. Devices, methods, and various embodiments disclosed herein are only exemplary. The disclosed structural and functional features are intended to enable those skilled in the art to specifically embody various embodiments and are not intended to limit the scope of the present invention. The terms and sentences disclosed herein are for the purpose of easy-to-understand descriptions of various features of the disclosed invention and are not intended to limit the scope of the present invention.

When the present invention is described, if it is determined that detailed descriptions of known technology related to the present invention unnecessarily obscure the subject matter of the present invention, detailed descriptions thereof will be omitted.

Hereinafter, a multi-microorganism detection system according to an embodiment of the present invention will be described.

Figure 1:
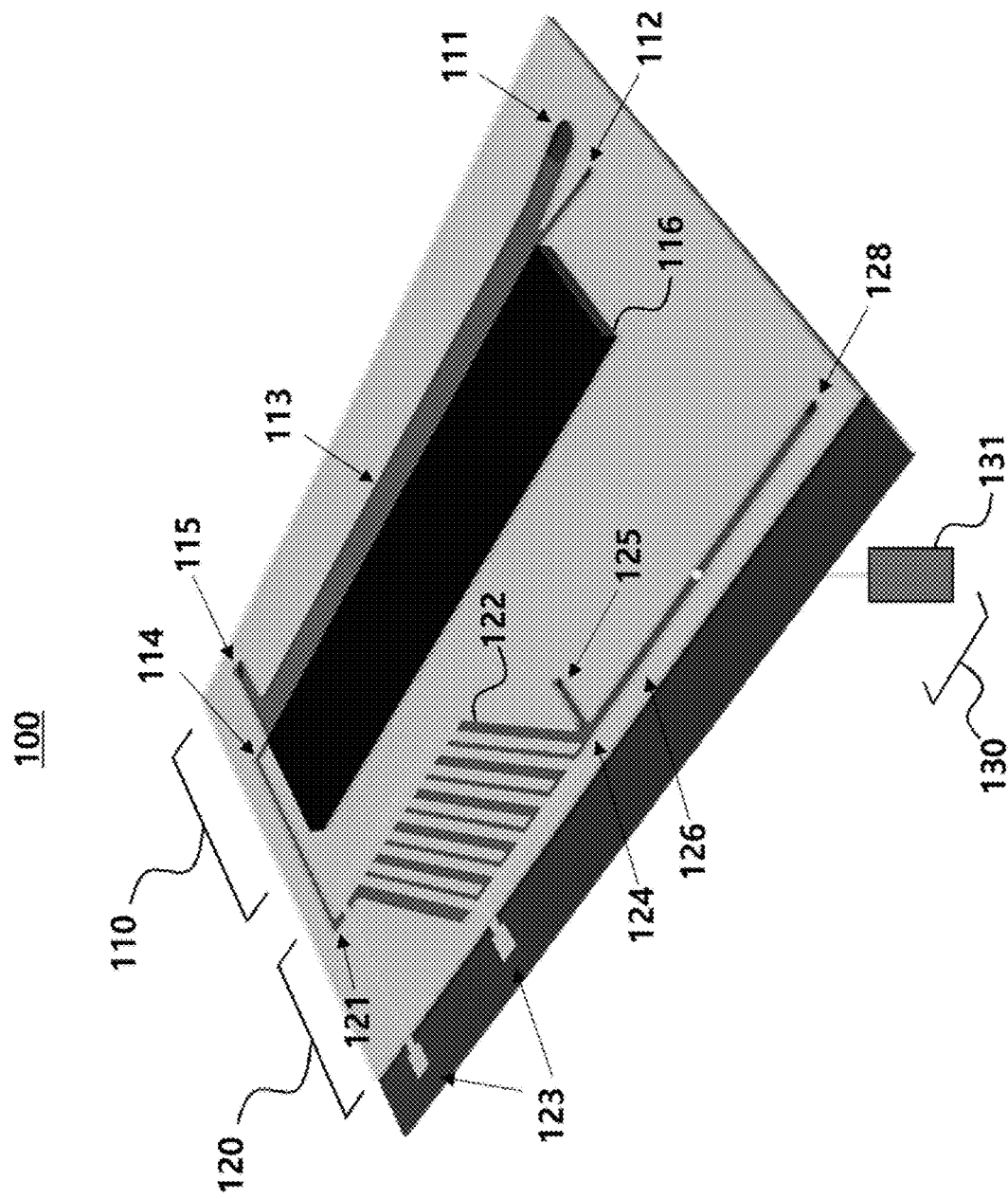
FIG. 1 is a view illustrating a multi-microorganism detection system according to an embodiment of the present invention.

FIG. 1 is a view illustrating a multi-microorganism detection system according to an embodiment of the present invention.

Referring to FIG. 1, the multi-microorganism detection system according to the embodiment of the present invention may include a concentration unit 110 including a magnetic member 116 for generating a magnetic force and configured to concentrate a magnetic particle-microorganism complex using the magnetic force, a separation unit 120 configured to separate magnetic particles from the magnetic particle-microorganism complex using the magnetic force and a dielectrophoresis (DEP) force, and a detection unit 130 configured to detect the magnetic particle-microorganism complex using a fluorescence signal of the magnetic particles. The components may be disposed on an upper surface of a plate.

The multi-microorganism detection system according to the embodiment of the present invention may further include a case in which the components may be disposed and may further include an output unit capable of visually and/or audibly displaying information about at least one of a type and concentration of the detected microorganism. Such an output unit may be composed of a speaker, a display device, or a combination thereof. The display device may include a liquid crystal display (LCD), a thin-film-transistor liquid-crystal display (TFT LCD), an organic light-emitting diode (OLED), a flexible display, a three-dimensional (3D) display, or an electronic ink (e-ink) display, and the output unit may receive information from a control unit and display the received information.

In the multi-microorganism detection system of the present invention, the concentration unit 110 may concentrate a microorganism complex bound to a magnetic particle and transmit the concentrated magnetic particle-microorganism complex to the separation unit 120.

In an embodiment, the magnetic particle bound to a microorganism may be a fluorescent magnetic particle, and the multi-microorganism detection system of the present invention may simultaneously detect several types of microorganisms by analyzing a fluorescence signal of a fluorescent magnetic particle bound to a specific microorganism.

Figure 2:
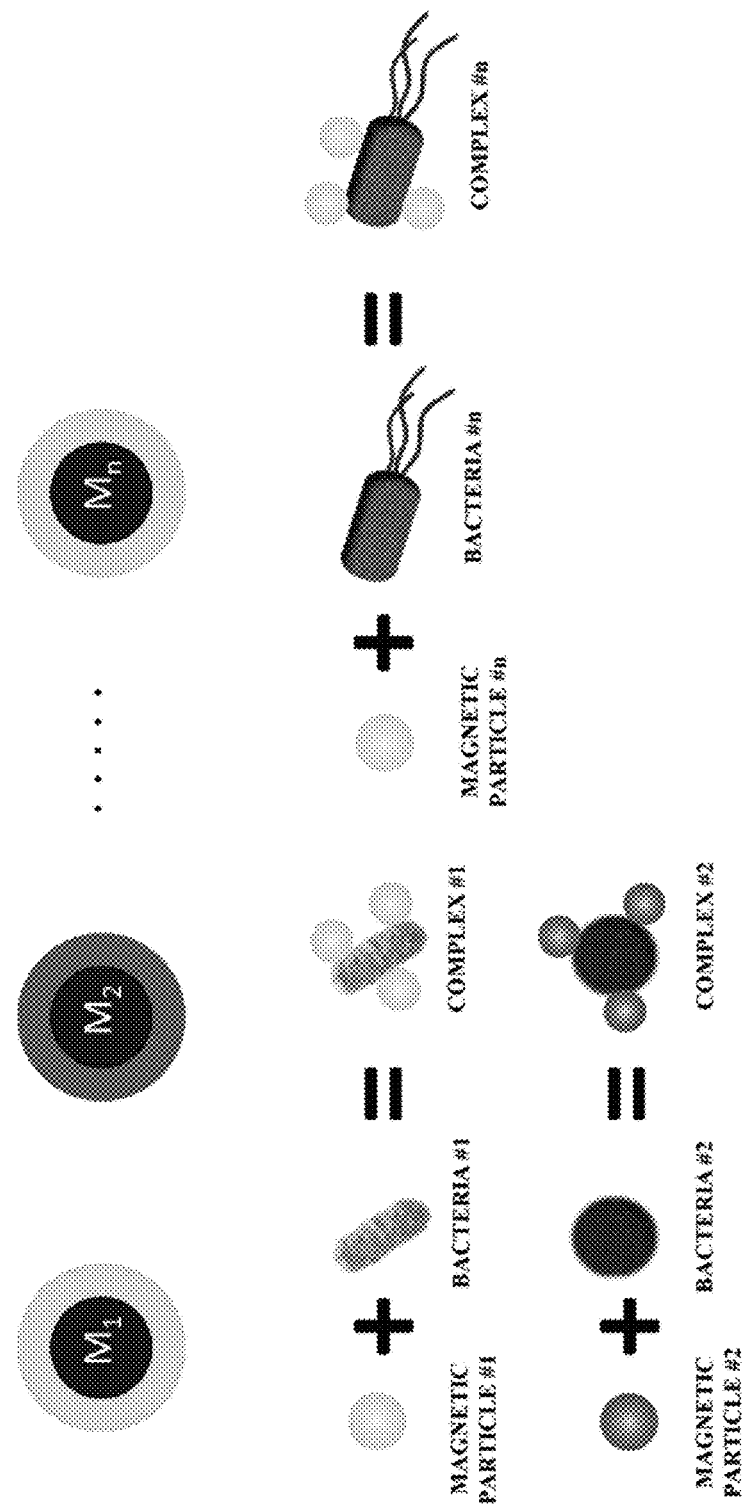
FIG. 2 is a schematic view illustrating a method of synthesizing a magnetic particle-microorganism complex of the present invention.

FIG. 2 is a schematic view illustrating a method of synthesizing the magnetic particle-microorganism complex of the present invention.

In the present invention, magnetic particles that exhibit a fluorescence signal may be synthesized and utilized with microorganisms, various types of magnetic particles $M_1$, $M_2$, ..., $M_n$ may be used as the magnetic particles, and the magnetic particles exhibit fluorescence signals in different wavelength bands. Therefore, magnetic particles that exhibit different wavelength bands may be bound to microorganisms according to types of microorganisms, and multiple types of microorganisms may be simultaneously detected through measurement/analysis of fluorescence signals.

Specifically, the fluorescent magnetic particle includes a fluorescent dye, which develops color at a specific wavelength, and Protein A. The Protein A is fixed onto a surface of the fluorescent magnetic particle by a covalent bond. The Protein A on the surface of the particle has high specificity and strong affinity with an antibody. The antibody bound to the Protein A is bound to a specific microorganism so that a fluorescent magnetic particle-microorganism complex is formed.

In an embodiment, the concentration unit 110 may include a first injection unit 111, a second injection unit 112, a concentration channel 113, a first discharge unit 114, a second discharge unit 115, and a magnetic member 116.

The first injection unit 111 and the second injection unit 112 may be coupled to one end portion of the concentration channel 113, and the first discharge unit 114 and the second discharge unit 115 may be coupled to the other end portion of the concentration channel 113.

The first injection unit 111 may inject a sample solution containing a complex in which magnetic particles and microorganisms are bound, and the second injection unit 112 may inject a sheath fluid.

The injected sample solution and sheath fluid may be mixed at an inlet of the concentration channel 113, and thus the concentration channel 113 may move the sheath fluid containing the magnetic particle-microorganism complex to the discharge units 114 and 115.

The first discharge unit 114 may transmit the sheath fluid containing the magnetic particle-microorganism complex that has moved through the concentration channel 113 to the separation unit 120, and the second discharge unit 115 may discharge the sample solution excluding the magnetic particle-microorganism complex to the outside of the system.

The magnetic member 116 may be disposed parallel to one side surface of the concentration channel 113 and may generate a magnetic force in the magnetic particles bound to the microorganisms. Accordingly, the complex in which the magnetic particles and the microorganisms are bound may be moved along one side surface of the concentration channel 113 due to the magnetic force acting on the magnetic particles.

As illustrated in FIG. 1, the magnetic member 116 may have a rectangular parallelepiped shape, but the shape may be easily selected by a person embodying the present invention. The lengths of the magnetic member 116 and the concentration channel 113 are preferably the same, and the concentration unit 110 and the separation unit 120 are disposed in parallel at a predetermined interval with the magnetic member 116 interposed therebetween. The interval is preferably a distance at which the magnetic force of the magnetic member 116 may cause an affect.

In an embodiment, the concentration unit 110 may be manufactured with a polyethylene tube and a polydimethylsiloxane (PDMS) channel using soft-lithography.

The separation unit 120 may use the magnetic force acting on the microorganism complex transmitted from the concentration unit 110 and a DEP force corresponding to the magnetic force to separate magnetic particles that cannot form the complex with the microorganism from the magnetic particle-microorganism complex.

In an embodiment, the separation unit 120 may include a third injection unit 121, a separation channel 122, an electrode unit 123, and a third discharge unit 124, and the separation unit 120 may further include a fourth discharge unit 125 that transmits the separated magnetic particle-microorganism complex to a detection channel.

The third injection unit 121 may inject the sheath fluid containing the magnetic particle-microorganism complex transmitted from the concentration unit 110 by the first discharge unit 114.

The third injection unit 121 and the first discharge unit 114 are located parallel to both side surfaces of the magnetic member 116 interposed therebetween, connected by a connection tube made of the same material as the third injection unit 121 and the first discharge unit 114, and are implemented so that flow directions of fluids are opposite to each other. Specifically, the connection tube may also be manufactured with a polyethylene tube and a PDMS channel using soft-lithography.

That is, the connection tube may be installed to surround an outer circumference of the magnetic member 116, and the sheath fluid containing the magnetic particle-microorganism complex discharged by the first discharge unit 114 is injected into the third injection unit 121 along the connection tube in a direction opposite to the discharge direction.

The sample solution injected from the first injection unit 111 contains not only the magnetic particle-microorganism complex but also the magnetic particles that cannot form the complex with the microorganism.

In the concentration unit 110, only the magnetic force is formed by the magnetic member 116, and thus it is not possible to separate the magnetic particles that cannot form the complex with the microorganism from the magnetic particle-microorganism complex. However, in the separation unit 120, by additionally forming the DEP force by the electrode unit 123, it is possible to separate the magnetic particles that cannot form the complex with the microorganism from the magnetic particle-microorganism complex.

Through the separation channel 122, the magnetic particles that cannot form the complex with the microorganism and the magnetic particle-microorganism complex may be moved together with the sheath fluid.

One end of the separation channel 122 may be coupled to the third injection unit 121, and the other end of the separation channel 122 may be coupled to the third discharge unit 124 and the fourth discharge unit 125. In this case, a width of the separation channel 122 may be increased in a direction from one end of the separation channel 122 and then decreased in a direction toward the other end. That is, the width of the separation channel 122 is increased in a direction from the third injection unit 121 toward an intermediate portion of the separation channel 122 and then is decreased in a direction from the intermediate portion toward the third discharge unit 124 and the fourth discharge unit 125.

In an embodiment, the separation unit 120 may be manufactured with a polyethylene tube and a PDMS channel using soft-lithography.

Referring to FIG. 1, in the embodiment of the present invention, the separation channel 122 has one side having a quadrilateral shape, more preferably, a parallelogrammic shape, which is disposed parallel to the magnetic member, the third injection unit 121 is coupled to an end portion of one side of the separation channel 122 close to the magnetic member, and the third discharge unit 124 and the fourth discharge unit 125 are coupled to the separation channel 122 at a diagonal position of the third injection unit 121.

The concentration channel 113 and the separation channel 122 may be located parallel to both side surfaces of the magnetic member 116 interposed therebetween.

The fourth discharge unit 125 extends to a detection channel 126, and the magnetic particle-microorganism complex separated in the separation channel 122 is moved along the detection channel 126 to the detection unit 130.

Figure 3A:
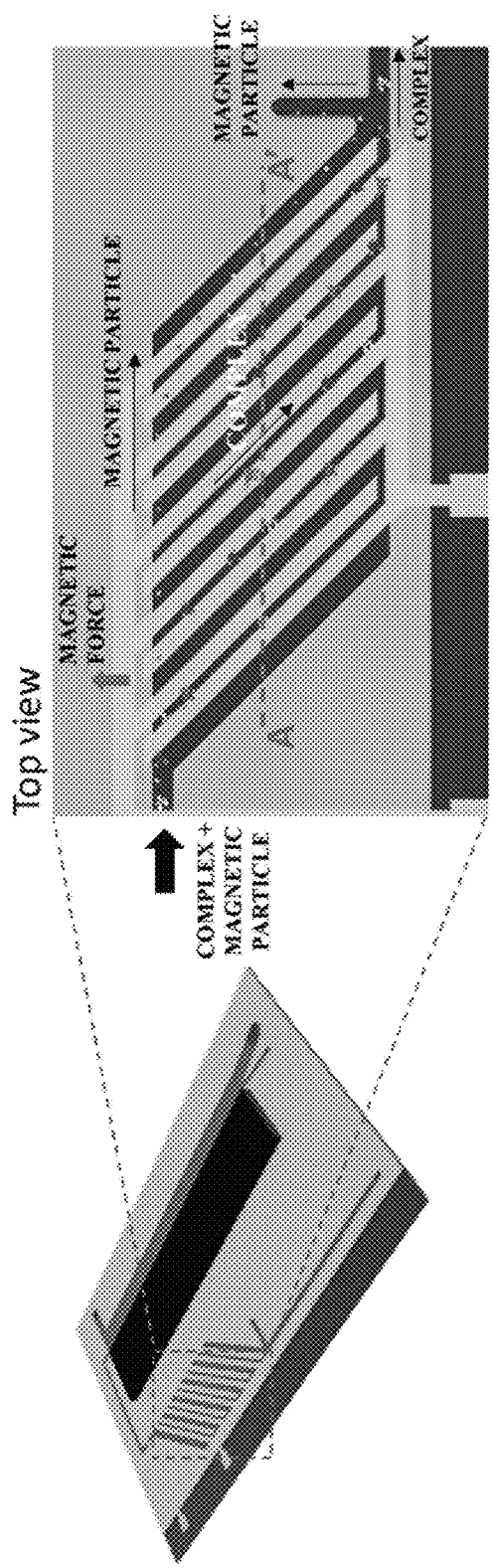
FIGS. 3A and 3B are an enlarged view and a cross-sectional view of a separation channel according to an embodiment of the present invention.
Figure 3B:
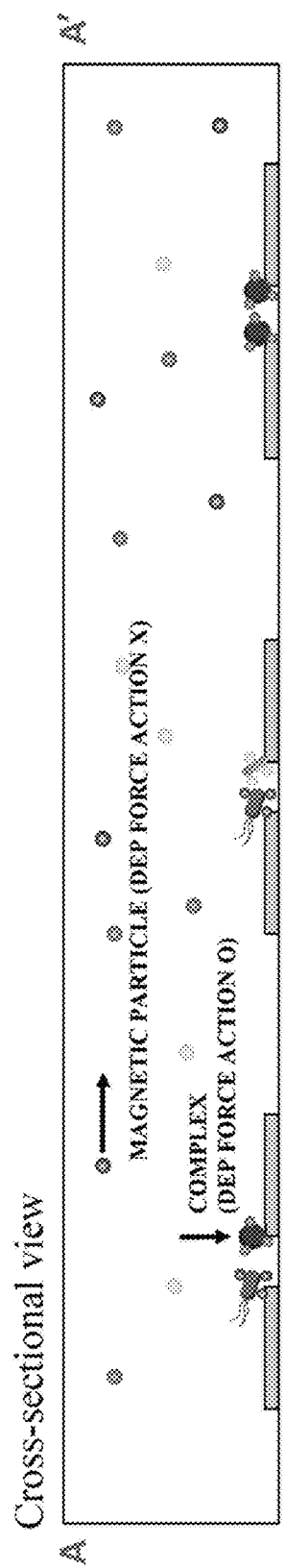

FIGS. 3A and 3B are an enlarged view and a cross-sectional view of the separation channel 122.

In the sample concentrated by the concentration unit 110, not only the complex (fluorescent particles+microorganism) but also the fluorescent magnetic particles that cannot form the complex with the microorganisms may be present together. Since the fluorescent magnetic particles that cannot form the complex may cause a measurement error when a concentration of the microorganisms in the sample is optically detected, a process of separating the fluorescent magnetic particles that cannot form the complex is required before transmitting the sample to the detection unit.

Referring to FIG. 3A, a patterned electrode may be formed below the separation channel 122, and the electrode may be formed on a plate of the multi-microorganism detection system using microelectromechanical systems (MEMS) processes with a thin film conductor such as platinum, gold, or chromium.

The patterned electrode of the separation channel 122 may be patterned while forming a predetermined angle (within 90 degrees) with the injection direction of the magnetic particle-microorganism complex and, preferably, may be patterned below the separation channel 122 to be parallel to a side of the separation channel 122 that is not parallel to the magnetic member.

The electrode unit 123 may generate an alternating current (AC) signal to apply the AC signal to the patterned electrode, generate a DEP force corresponding to the magnetic particle-microorganism complex according to a frequency of the AC signal, and use the DEP force to separate the fluorescent magnetic particles from the complex.

In the separation channel 122, no DEP force is generated in the fluorescent magnetic particles that cannot form the complex, only the magnetic force due to the magnetic member acts, and thus, due to the magnetic force, the fluorescent magnetic particles are moved along a wall surface of the separation channel 122 adjacent to the magnetic member 116 and then separated and discharged to the fourth discharge unit 125. The fourth discharge unit 125 is formed perpendicular to the detection channel 126 in a direction in which the magnetic member 116 is present, and thus the magnetic particles are moved along one side of the separation channel 122 located parallel to the magnetic member 116 and is moved to the fourth discharge unit 125.

Referring to FIG. 3B, the microorganism complex bound to the fluorescent magnetic particles is moved along the electrode in a sensor direction due to the DEP force and is discharged to the third discharge unit 124. Only the complex may be selectively separated and moved using a frequency condition of the AC signal applied to the electrode.

FIG. 3B is a view illustrating a DEP force according to an embodiment of the present invention.

In this case, for example, the magnetic force acting on the magnetic particles bound to the microorganism complex may be expressed as Equation 1 below.

$$\vec{F}_{Mag} = 2\pi \mu_m K(\mu_m, \mu_p) \alpha^3 \nabla |\overline{H}_{ext}(\vec{r}_0)^2|$$ [Equation 1]

Here, $\vec{F}_{Mag}$ denotes the magnetic force, $\mu_m$ denotes the permeability of the medium, $K(\mu_m, \mu_p)$ denotes the Clausius-Mossotti (CM) factor, $\mu_p$ denotes the permeability of a particle, $\alpha$ denotes a radius of a particle, $\overline{H}_{ext}$ denotes a magnetic field, and $\vec{r}_o$ denotes a position vector.

The separation channel 122 may be designed to have a structure in which a width is gradually increased so that a velocity of a fluid that moves through the separation channel 122 may be gradually reduced.

In this case, in the separation channel 122 for reducing the flow velocity, a force acting on the microorganisms may include a drag force and a DEP force. Here, the drag force may be increased in proportion to the flow velocity, and when the drag force is high, the microorganisms may not be separated due to the DEP force and may flow along the fluid.

Therefore, it may be necessary to reduce the drag force in order to separate the microorganisms using the DEP force. In this case, the separation channel 122 according to the present invention may reduce the velocity of the fluid by gradually increasing the width of the corresponding channel, thereby reducing the drag force.

For example, the drag force and the DEP force according to the width structure of the separation channel 122 may be expressed as Equation 2 and Equation 3 below, respectively.

$$\vec{F}_d = 6\pi \eta \alpha \overline{U}$$ [Equation 2]

Here, $\vec{F}_d$ denotes the drag force, $\eta$ denotes the viscosity of the medium, $\alpha$ denotes the radius of a particle, and $\overline{U}$ denotes the flow velocity of fluid.

$$F_{DEP} = 2\pi \varepsilon_m r^3 Re[\underline{K}(\omega)] \cdot \nabla |\underline{E}(r)|^2$$ [Equation 3]

Here, $F_{DEP}$ denotes the DEP force, $\varepsilon_m$ denotes the permittivity of the medium, r denotes the radius of particles, $K(\omega)$ denotes the CM factor, and $\underline{E}(r)$ denotes the electric field.

Due to the reduced drag force and DEP force, the magnetic particle-microorganism complex is moved along the edge of the electrode while being attracted to an edge portion of the patterned electrode located below the separation channel 122.

The width of the separation channel 122 is reduced in a direction toward the discharge units 124 and 125. The flow velocity is increased due to the reduced width of the separation channel 122, and thus the reduced drag force is increased again. The increased drag force may allow the magnetic particle-microorganism complex attracted to the edge portion of the electrode to be transmitted to the discharge units 124 and 125.

The magnetic particle-microorganism complex separated in the separation channel 122 is moved to the third discharge unit 124 and is moved to the detection channel 126 extending to the third discharge unit 124.

A fifth discharge unit 127 is located at an end of the detection channel 126, and the detection unit 130 for optically detecting the magnetic particle-microorganism complex is located between the detection channel 126 and the fifth discharge unit 127. Therefore, the magnetic particle-microorganism complex separated in the separation channel 122 is moved to the detection channel 126, passes through the detection unit 130, and is discharged to the outside through the fifth discharge unit 127.

In an embodiment, the detection channel 126 may be manufactured with a polyethylene tube and a PDMS (polydimethylsiloxane) channel using soft-lithography.

Figure 4:
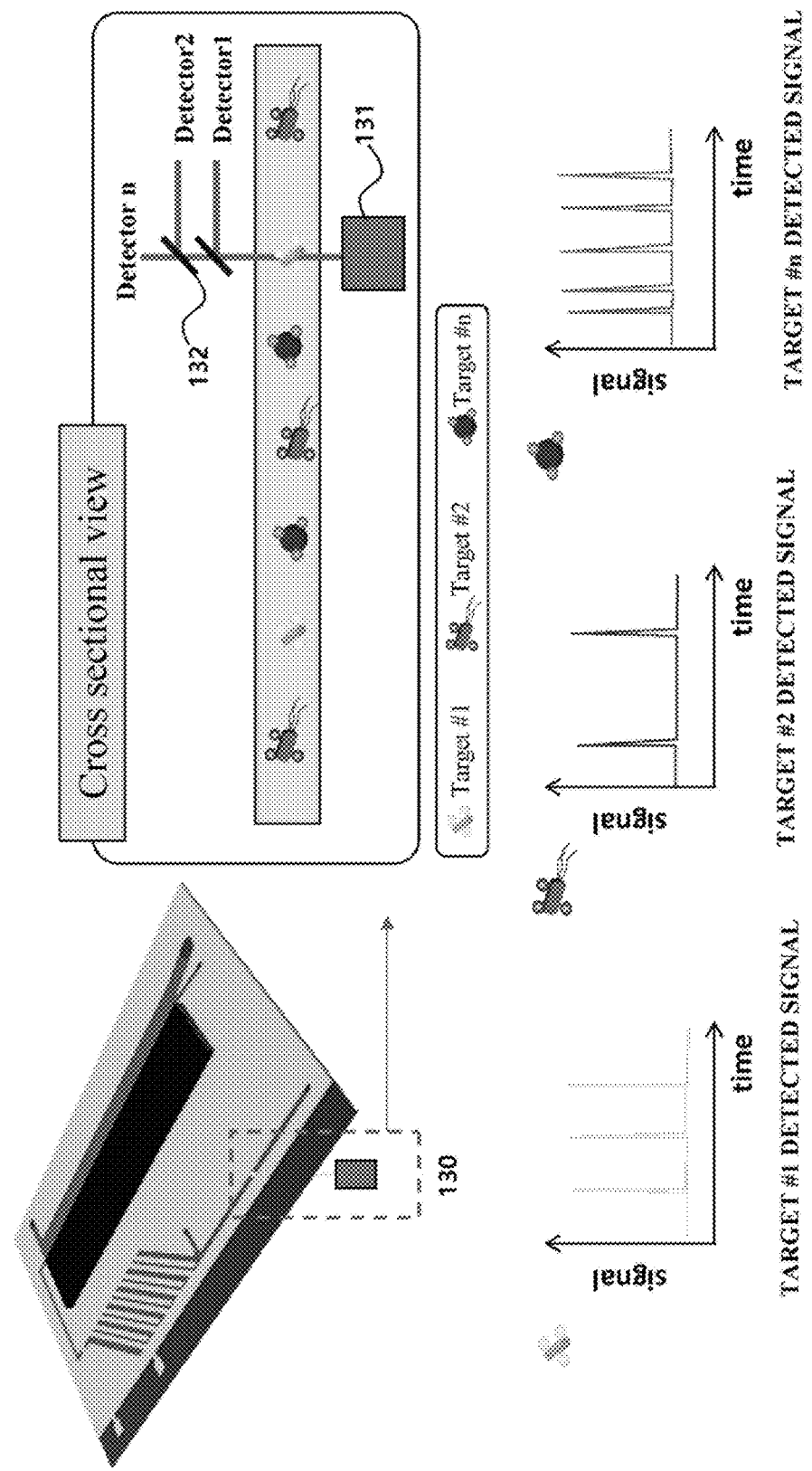
FIG. 4 is a schematic view illustrating a detection unit according to an embodiment of the present invention and examples thereof.

Referring to FIG. 4, the detection unit 130 may include a light source 131 for exciting a fluorescent marker of the fluorescent magnetic particle and photodetectors 132 for detecting emitted light. Specifically, the light source is a light source such as a light-emitting diode (LED).

The detection channel 126 and the detection unit 130 are disposed to intersect each other, the light source 131 is located below the detection channel 126, and the photodetectors 132 capable of detecting light emitted by the magnetic particle-microorganism complex in the detection channel 126 are located above the detection channel 126.

The microorganisms are bound to fluorescent markers having different emission wavelength bands depending on the types thereof, and each photodetector 132 is configured together with a filter for detecting a specific optical signal in order to accurately detect the emitted light. The optical signal may include properties such as fluorescence, light absorbance, chemiluminescence, optical scattering (e.g., Rayleigh scattering, Mie scattering, and Raman scattering), imaging, transmittance, a particle size, the number of particles, turbidity, and combinations thereof.

Therefore, when the magnetic particle-microorganism complex passes through the detection unit 130 while being moved along the detection channel 126, different signals are generated depending on the type of microorganism, and the photodetector 132 may detect the different signals to measure the types and concentration of the microorganisms.

Graphs at the bottom of FIG. 4 are views showing examples of magnetic particle-microorganism complexes detected using the photodetectors 132 according to an embodiment of the present invention.

Different wavelengths of light emitted from the magnetic particle-microorganism complexes may be separated by an optical filter prior to detection by the photodetectors 132, and different optical signals separated by the optical filter may be detected by the plurality of corresponding photodetectors 132.

Therefore, by analyzing the optical signal measured by each photodetector 132, it is possible to measure the individual concentration of each microorganism together with the type of microorganism and, accordingly, it is possible to simultaneously detect various microorganisms present in the sample.

The configuration of the detection unit 130 may be easily selected by those skilled in the art.

The multi-microorganism detection system may further include a control unit (not illustrated).

In an embodiment, the control unit may include at least one processor or a microprocessor or may be a part of a processor. The control unit may control the operation of the multi-microorganism detection system 100 according to various embodiments of the present invention.

The control unit may include a signal generator, control the behavior of microorganisms through the DEP force, analyze electrical signals generated from the photodetectors, measure the concentration of the microorganisms in the sample by counting peaks generated by the microorganisms from the measured signal results, and display the measured concentration on a display.

The control unit may measure the concentration of the microorganisms in the sample using a calibration curve according to the concentration and using the detected electrical signals and display the measured concentration on the display.

The control unit may supply power required to each component of the microorganism detection system and include a direct current (DC) signal generator and an AC signal generator.

The AC signal generator may apply an AC signal to the electrode unit 123 of the separation channel 122 to separate the microorganism complex using the DEP force.

The present invention relates to a rapid and accurate multi-microorganism detection system. Microorganisms can be concentrated at a high throughput using DEP after synthesizing the microorganisms and a fluorescent magnetic particle, and when a complex in which the fluorescent magnetic particle is bound to the microorganism passes through a detection unit by moving only the microorganism to the detection unit after separating the magnetic particle from the complex (i.e., the microorganism to which the magnetic particle is bound) using a DEP force, a fluorescence signal of a specific wavelength band can be generated according to the type of the fluorescent magnetic particle and the concentration of the microorganism according to the type of microorganism can be measured by measuring and analyzing the fluorescence signal.

Effects of the present invention are not limited to the above-described effects, and potential effects expected by the technical features of the present invention may be clearly understood from the above detailed description.

The above-described embodiments are only examples and it will be understood by those skilled in the art that various modifications and alterations may be made without departing from the spirit and scope of the invention.

Therefore, the embodiments disclosed in this specification should be considered in a descriptive sense only and not for purposes of limitation. Accordingly, the scope of the invention is not limited by the embodiments.

The scope of the invention is defined by the appended claims and encompasses all modifications and equivalents that fall within the scope of the appended claims.

What is claimed is:

1. A multi-microorganism detection system comprising:
a concentration unit positioned on a first area of the multi-microorganism detection system, and configured to concentrate a magnetic particle-microorganism complex, by using a magnetic force generated by a magnetic member included in the concentration unit;
a separation unit positioned on a second area of the multi-microorganism detection system, and configured to separate magnetic particles from the magnetic particle-microorganism complex, by using the magnetic force and a dielectrophoresis (DEP) force generated by an electrode included in the separation unit; and
a detection unit positioned on a third area of the multi-microorganism detection system, and configured to detect the magnetic particle-microorganism complex, by using a fluorescence signal of the magnetic particles,
wherein the first area, the second area, and the third area of the multi-microorganism detection system are separated in a plan view, from each other.

2. The multi-microorganism detection system of claim 1, wherein the concentration unit includes:
a first injection unit configured to inject a sample solution containing the magnetic particles and the magnetic particle-microorganism complex;
a second injection unit configured to inject a sheath fluid;
a concentration channel through which the sheath fluid containing the magnetic particle-microorganism complex is moved;
a first discharge unit configured to transmit the sheath fluid containing the magnetic particle-microorganism complex to the separation unit, though a connecting channel that connects the concentration unit and the separation unit; and
a second discharge unit configured to discharge the sample solution.

3. The multi-microorganism detection system of claim 2, wherein the concentration channel is located parallel to the magnetic member, and
the magnetic particle-microorganism complex is moved along one side surface of the concentration channel due to the magnetic force.

4. The multi-microorganism detection system of claim 1, wherein the separation unit includes:
a third injection unit configured to inject a sheath fluid containing the magnetic particles and the magnetic particle-microorganism complex, wherein the sheath fluid is received through a connecting channel that connects the concentration unit and the separation unit;
a separation channel through which the magnetic particles and the magnetic particle-microorganism complex are moved;
a third discharge unit configured to discharge the separated magnetic particles; and
a fourth discharge unit configured to transmit the separated magnetic particle-microorganism complex to a detection channel.

5. A multi-microorganism detection system comprising:
a concentration unit including a magnetic member for generating a magnetic force and configured to concentrate a magnetic particle-microorganism complex using the magnetic force;
a separation unit configured to separate magnetic particles from the magnetic particle-microorganism complex using the magnetic force and a dielectrophoresis (DEP) force; and
a detection unit configured to detect the magnetic particle-microorganism complex using a fluorescence signal of the magnetic particles,
wherein the separation unit includes:
a third injection unit configured to inject a sheath fluid containing the magnetic particles and the magnetic particle-microorganism complex;
a separation channel through which the magnetic particles and the magnetic particle-microorganism complex are moved;
a third discharge unit configured to discharge the separated magnetic particles; and
a fourth discharge unit configured to transmit the separated magnetic particle-microorganism complex to a detection channel, and
wherein:
one end of the separation channel is coupled to the third injection unit;
the other end of the separation channel is coupled to the third discharge unit and the fourth discharge unit; and a width of the separation channel is increased in a direction from the one end thereof and then is decreased in a direction toward the another end.

6. A multi-microorganism detection system comprising:

a concentration unit including a magnetic member for generating a magnetic force and configured to concentrate a magnetic particle-microorganism complex using the magnetic force;

a separation unit configured to separate magnetic particles from the magnetic particle-microorganism complex using the magnetic force and a dielectrophoresis (DEP) force; and a detection unit configured to detect the magnetic particle-microorganism complex using a fluorescence signal of the magnetic particles, wherein the separation unit includes:

a third injection unit configured to inject a sheath fluid containing the magnetic particles and the magnetic particle-microorganism complex;

a separation channel through which the magnetic particles and the magnetic particle-microorganism complex are moved;

a third discharge unit configured to discharge the separated magnetic particles; and a fourth discharge unit configured to transmit the separated magnetic particle-microorganism complex to a detection channel, and wherein the separation channel has one side having a quadrilateral shape which is disposed parallel to the magnetic member, the third injection unit is coupled to an end portion of one side of the separation channel close to the magnetic member, and the third discharge unit and the fourth discharge unit are coupled to the separation channel at a diagonal position of the third injection unit.

7. The multi-microorganism detection system of claim 4, wherein the third discharge unit and the fourth discharge unit are vertically located at the other end of the separation channel.

8. The multi-microorganism detection system of claim 4, wherein the electrode is located below the separation channel.

9. The multi-microorganism detection system of claim 8, wherein the electrode is patterned while forming a predetermined angle with an injection direction of the magnetic particle-microorganism complex in the separation channel.

* * * * *